United States Patent [19]

Gutierrez

[11] Patent Number: 4,956,354
[45] Date of Patent: Sep. 11, 1990

[54] THERAPEUTIC PREPARATION FOR USE ON SKIN

[75] Inventor: Gregoria Gutierrez, Ibague, Colombia

[73] Assignees: Thomas G. Kottke; Mary L. Kottke, both of Marrysville, Pa.

[21] Appl. No.: 280,384

[22] Filed: Dec. 6, 1988

[51] Int. Cl.$^5$ .................... A61K 31/635; A61K 47/00
[52] U.S. Cl. ................... 514/157; 424/195.1; 424/642
[58] Field of Search .............. 514/156, 157, 158, 770, 514/777; 424/DIG. 5, 49, 59

[56] References Cited

U.S. PATENT DOCUMENTS

| | | | |
|---|---|---|---|
| 4,151,304 | 4/1979 | Evans | 514/770 |
| 4,659,562 | 4/1987 | Arraudeau et al. | 514/770 |
| 4,713,242 | 12/1987 | Treuzeluk | 424/642 |
| 4,765,922 | 8/1988 | Contamin et al. | 424/DIG. 5 |

FOREIGN PATENT DOCUMENTS 0177920 7/1985 Japan.

OTHER PUBLICATIONS

*Pharmaceutical Formulas*, vol. II, pp. 84 and 85, 1946.

Primary Examiner—Douglas W. Robinson
Assistant Examiner—Kevin E. Weddington
Attorney, Agent, or Firm—Allan B. Osborne

[57] ABSTRACT

A therapeutic preparation for the treatment of skin problems. More particularly, the preparation is a mixture including almond oil, sulfathiazole, water and paraffin wax.

4 Claims, No Drawings

THERAPEUTIC PREPARATION FOR USE ON SKIN

FIELD OF THE INVENTION

This invention relates to a preparation useful in the treatment of damaged skin and, more particularly, on burns to the skin.

BACKGROUND OF THE INVENTION

Burns to the skin are instantly painful, even in cases of minor first degree burns. Accordingly, workers in the field have throughout the years, been experimenting and developing ointments, preparations and mixtures which can be quickly applied to the affected areas to give both immediate relief and provide rapid healing. One such mixture disclosed in U.S. Pat. No. 4,713,242 includes the extract from the dried leaves of the Eupatorium plant, sulfathiazole, zinc oxide and petrolatum.

Other prior art patents disclosing therapeutic mixtures for treating burns include U.S. Pat. No. 4,049,802 disclosing an admixture of silver sulfadiazine and zinc sulfadiazine, and U.S. Pat. No. 4,078,058 disclosing compositions containing cerium sulfadiazine.

The above cited prior art patents do not appear to disclose a therapeutic preparation which includes almond oil and sulfathiazole.

The object of the present invention is to provide a therapeutic preparation for the almost instantaneous relief of pain from burns to the skin. It is a further object of the present invention to provide a therapeutic preparation that does not irritate the skin and which promotes rapid healing of first and second degree burns without side effects.

A further object of the present invention is to provide a therapeutic preparation useful for treating insect stings and bites, abrasions and other like injuries to the skin.

SUMMARY OF THE INVENTION

According to the present invention, a therapeutic preparation for alleviation of burns and other injuries to the skin comprises almond oil, sulfathiazole, water and paraffin wax.

DETAILED DESCRIPTION OF THE INVENTION

The following example illustrates a suitable therapeutic preparation containing almond oil:

| EXAMPLE | |
|---|---|
| COMPONENT | AMOUNT |
| Expressed almond oil | 4 fluid ounces |
| Sulfathiazole | 2 grams |
| Water | 0.3 fluid ounces |
| Paraffin wax | 5 grams |

In this example, the components may be blended together according to the following method. The sulfathiazole is dissolved in the water and then added to the almond oil. This mixture is heated to the boiling point of water to remove any excess water therein. The wax is then added to the hot mixture and stirred until dissolved. Upon cooling, the mixture forms a light yellow-to-white jelly.

A substantial number of preparations, according to the present invention, has been tested on humans by being applied directly to the burn area. No toxic or other adverse side effects have been reported. Preferably, the treated area should not be covered with a cloth or bandages. The results demonstrate a very effective treatment with almost instantaneous relief of pain and rapid healing.

Further, although the disclosed preparation is particularly effective on burns, other injuries, e.g., common skin rashes, abrasions, insect bites and stings, may also be treated.

Although sulfathiazole is preferred, other heterocyclic sulfa drugs may be used.

While the therapeutic preparation, according to the present invention, has been described by means of a specific example, it will be apparent to those skilled in the art that modifications are possible within the spirit and scope of the disclosed principle.

What I claim is:

1. A therapeutic composition for treating burns and other skin injuries, consisting of;
   almond oil, sulfathiazole, water and paraffin wax;
   wherein the proportions of each of 4 fluid ounces of almond oil, 2 grams of sulfathiazole, 0.3 fluid ounces of water and 5 grams of paraffin wax.

2. The therapeutic preparation of claim 1 wherein said almond oil is expressed.

3. A method for preparing a therapeutic composition comprising almond oil, sulfathiazole, water and paraffin wax, said method consiting of the steps of:
   a. dissolving 2 grams of sulfathiazole in 0.3 fluid ounces of water;
   b. adding the mixture of step a. to 4 fluid ounces of almond oil;
   c. heating the mixture of step b. to the boiling point of water to drive off excess water;
   d. adding 5 grams of paraffin wax to the mixture of step c. while still hot and stirring to dissolve the wax therein; and
   e. cooling the mixture of step d.

4. A method of treating burn and skin injuries which comprises topically applying to the affected ara a therapeutically effective amount of a composition of claim 1.

* * * * *